(12) United States Patent
Konno (10) Patent No.: US 7,561,351 B2
(45) Date of Patent: Jul. 14, 2009

(54) IMAGING MODULE FOR ENDOSCOPES (75) Inventor: Mitsujiro Konno, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 1 day.

(21) Appl. No.: 11/897,292

(22) Filed: Aug. 29, 2007

(65) Prior Publication Data

US 2008/0055748 A1    Mar. 6, 2008

(30) Foreign Application Priority Data

Sep. 1, 2006   (JP)   ............................. 2006-237732

(51) Int. Cl.
*G02B 7/02*   (2006.01)
*G02B 21/02*   (2006.01)

(52) U.S. Cl. ..................... 359/811; 359/819; 359/656

(58) Field of Classification Search ......... 359/656–661, 359/811, 819–822

See application file for complete search history.

(56) References Cited

U.S. PATENT DOCUMENTS

| | | | | |
|---|---|---|---|---|
| 6,618,207 B2 * | 9/2003 | Lei | ............................. | 359/656 |
| 6,956,703 B2 * | 10/2005 | Saito | .......................... | 359/660 |
| 7,093,945 B2 * | 8/2006 | Suga | .......................... | 359/614 |

FOREIGN PATENT DOCUMENTS

| | | |
|---|---|---|
| JP | 2003-260023 | 9/2003 |
| WO | WO 02/054932 | 7/2002 |

\* cited by examiner

*Primary Examiner*—Mohammed Hasan
(74) *Attorney, Agent, or Firm*—Kenyon & Kenyon LLP (57) ABSTRACT An imaging module for endoscopes includes a convex lens and an image sensor in which mutual positions are fixed and a plurality of optical modules that are selectively mountable with respect to the fundamental module so that the observation condition is switched in accordance with an optical module selectively mounted. The imaging module for endoscopes is constructed so that when each of the optical modules is mounted to the fundamental module, an image position and an angle of oblique incidence of light of an observation image on the image sensor are practically unchanged.

4 Claims, 10 Drawing Sheets

IMAGING MODULE FOR ENDOSCOPES

This application claims benefits of Japanese Application No. 2006-237732 filed in Japan on Sep. 1, 2006, the contents of which are incorporated herein by reference.

BACKGROUND OF THE INVENTION

1. Field of the Invention

This invention relates to an imaging module for endoscopes that is suitable for the production of an endoscope premised on a disposable device, such as a capsule endoscope.

2. Description of Related Art

Recently, in the diagnosis of the digestive tract or others in a living body, a capsule endoscope in which an insertion part is eliminated so that a person to be diagnosed can be relieved from the pain of insertion of the insertion part has come into use.

As capsule endoscopes of this type, devices set forth, for example, in Japanese Patent Kokai No. 2003-260023 and PCT Publication No. WO 02/054932 A3 are known.

Such capsule endoscopes are premised on disposable devices. In general, as products of the same design used for disposable devices are mass-produced, production costs can be reduced.

However, in observation with the endoscope, for example, a field range required varies with the application of observation (a part to be observed) such as the stomach or the large intestine. It is thus necessary to provide endoscopes used as disposable devices in which an observation condition in the optimum field range is obtained in accordance with the difference of the application of observation (a part to be observed).

SUMMARY OF THE INVENTION

The imaging module for endoscopes according to the present invention has a fundamental module including a convex lens and an image sensor in which mutual positions are fixed and a plurality of optical modules that are selectively mountable with respect to the fundamental module so that the observation condition is switched in accordance with an optical module selectively mounted. The imaging module for endoscopes is constructed so that when each of the optical modules is mounted to the fundamental module, an image position and an angle of oblique incidence of light of an observation image on the image sensor are practically unchanged.

In the imaging module for endoscopes of the present invention, it is desirable that the plurality of optical modules have a first optical module including a first concave lens made of plastic and a first lens frame made of black resin, positioning and retaining the first concave lens; and a second optical module including, in order from the object side, a second concave lens made of plastic, a third concave lens constructed similar to the first concave lens, and a second lens frame made of black resin, positioning and retaining the second concave lens and the third concave lens, the second lens frame being constructed so that spacing between the image-side surface of the third concave lens and the object-side surface of the convex lens of the fundamental module where the second optical module is mounted to the fundamental module is different from spacing between the image-side surface of the first concave lens and the object-side surface of the convex lens of the fundamental module where the first optical module is mounted to the fundamental module, to be selectively mountable with respect to the fundamental module.

In the imaging module for endoscopes of the present invention, it is desirable that the plurality of optical modules have a first optical module including a first concave lens made of plastic and a first lens frame made of black resin, positioning and retaining the first concave lens; and a second optical module including a second concave lens constructed similar to the first concave lens and a second lens frame made of black resin, positioning and retaining the second concave lens, the second lens frame being constructed so that spacing between the image-side surface of the second concave lens and the object-side surface of the convex lens of the fundamental module where the second optical module is mounted to the fundamental module is different from spacing between the image-side surface of the first concave lens and the object-side surface of the convex lens of the fundamental module where the first optical module is mounted to the fundamental module, to be selectively mountable with respect to the fundamental module.

In the imaging module for endoscopes of the present invention, it is desirable that the plurality of optical modules have a first optical module including a first concave lens made of plastic and a first lens frame made of black resin provided with a first aperture stop, positioning and retaining the first concave lens; and a second optical module including a second concave lens constructed similar to the first concave lens and a second lens frame made of black resin provided with a second aperture stop different in location from the first aperture stop, to be selectively mountable with respect to the fundamental module.

According to the present invention, the imaging module for endoscopes is obtained in which image formation can be achieved on the optimum observation condition accommodating the application of observation (a part to be observed), the number of constituent parts is kept to a minimum, time for lens focus adjustment is unnecessary, the fabrication cost can be reduced as far as possible, and production efficiency can be improved.

These and other features and advantages of the present invention will become apparent from the following detailed description of the preferred embodiments when taken in conjunction with the accompanying drawings.

DETAILED DESCRIPTION OF THE PREFERRED EMBODIMENTS

Before undertaking the description of the embodiments, the function and effect of the present invention will be explained.

In the endoscope used as a disposable device like the capsule endoscope, it is desired that time required for focus adjustment in its fabrication is eliminated and a low cost is brought about. In order to achieve this, it becomes necessary that the rearmost lens (a lens located closest to the image sensor) constituting the imaging module used in the endoscope is constructed integrally with a flange and the length of the flange is designed with a high degree of accuracy so that the flange can be cemented directly to the substrate of the image sensor. It is thus necessary that the rearmost lens part cemented and fixed to the image sensor is fabricated with great accuracy and high-precision control is applied.

Generally, in plastic lenses made on the premise that mass production is performed, many dies (for example, four dies for four lenses) must be used in a single molding. It is also necessary that, in view of occurrence of die damage, spare dies of the same number as the above dies (four, therefore, eight in total) are prepared.

Here, if an attempt is made to further increase the number of kinds of lenses in accordance with the application of observation (a part to be observed), the number of dies multiplied by the number of kinds increased (for example, a total of 16 dies in the case of two kinds of lenses) will be needed and a control cost will be raised.

In order to reduce the cost of the entire imaging module, it is necessary to consider the reduction of the cost of the entire fabrication process particularly including, for example, the automation of assembly such as automation in the holding and transportation of an optical system. However, if the kind of optical system incorporated in the imaging module in accordance with the application of observation (a part to be observed) is increased to change the structure of the imaging module relative to the holding and transportation of the lens frame provided with the optical system, such automation becomes difficult. Thus, in the assembly of the imaging module, it is necessary to have the structure that is capable of switching observation conditions such as the field range (the field angle), the depth of field, and the F-number without practically changing the fundamental structure of the imaging module relative to the transportation.

Development of the image sensor combined in accordance with each individual optical system accommodating the application of observation (a part to be observed) causes an increase of the fabrication cost. It is thus desirable that any image sensor used in the fundamental module has a common specification. However, an angle of oblique incidence that an image can be picked up in a high sensitivity varies with an individual image sensor.

However, the imaging module for endoscopes of the present invention is constructed so that the fundamental module including the convex lens as the rearmost lens and the image sensor in which mutual positions are fixed can also be used in the fabrication of the imaging module that the application of observation (a part to be observed) is different, a plurality of optical modules are selectively mounted to the fundamental module with respect to the difference of the application of observation (a part to be observed) and thereby the observation condition is switched, and even when any of the optical modules is mounted to the fundamental module, the image position and the angle of oblique incidence of light of an observation image on the image sensor are practically unchanged.

By doing so, even when any optical module is mounted to the fundamental module, the image position of light of the observation image on the image sensor is almost the same, and thus the focus adjustment of the rearmost lens can be eliminated. Further, the number of lens parts can be kept to a minimum and the high-precision control is facilitated without increasing the control cost. Still further, the production efficiency is improved and the mass production is facilitated.

The fundamental structure of the imaging module relative to the holding and transportation of the lens frame requires little change to switch the observation condition, the automation of assembly is not obstructed, and the cost of the entire fabrication process can be reduced.

Even when any optical module is mounted to the fundamental module, the angle of oblique incidence of light of an observation image on the image sensor is practically unchanged. Hence, the fundamental module using the image sensor of a common specification can be combined with an optical module accommodating a different application of observation (a different part to be observed), and an increase of the fabrication cost caused by developing the image sensor combined in accordance with each individual optical system can be checked.

In the imaging module for endoscopes of the present invention, it is desirable that the plurality of optical modules have a first optical module including a first concave lens made of plastic and a first lens frame made of black resin, positioning and retaining the first concave lens; and a second optical module including, in order from the object side, a second concave lens made of plastic, a third concave lens constructed similar to the first concave lens, and a second lens frame made of black resin, positioning and retaining the second concave lens and the third concave lens, the second lens frame being constructed so that spacing between the image-side surface of the third concave lens and the object-side surface of the convex lens of the fundamental module where the second optical module is mounted to the fundamental module is different from spacing between the image-side surface of the first concave lens and the object-side surface of the convex lens of the fundamental module where the first optical module is mounted to the fundamental module, to be selectively mountable with respect to the fundamental module.

By doing so, the number of kinds of optical parts used in the assembly can be kept to a minimum and at the same time, the imaging module for endoscopes in which the field range varies with the application of observation can be fabricated.

In the imaging module for endoscopes of the present invention, it is desirable that the plurality of optical modules have a first optical module including a first concave lens made of plastic and a first lens frame made of black resin, positioning and retaining the first concave lens; and a second optical module including a second concave lens constructed similar to the first concave lens and a second lens frame made of black resin, positioning and retaining the second concave lens, the second lens frame being constructed so that spacing between the image-side surface of the second concave lens and the object-side surface of the convex lens of the fundamental module where the second optical module is mounted to the fundamental module is different from spacing between the image-side surface of the first concave lens and the object-side surface of the convex lens of the fundamental module where the first optical module is mounted to the fundamental module, to be selectively mountable with respect to the fundamental module.

By doing so, it is also possible to switch the imaging module for endoscopes to fabricate the imaging module for endoscopes in which the field range is the same, but the depth of field is different.

In the imaging module for endoscopes of the present invention, it is desirable that the plurality of optical modules have a first optical module including a first concave lens made of plastic and a first lens frame made of black resin provided with a first aperture stop, positioning and retaining the first concave lens; and a second optical module including a second concave lens constructed similar to the first concave lens and a second lens frame made of black resin provided with a second aperture stop different in location from the first aperture stop, to be selectively mountable with respect to the fundamental module.

By doing so, it is also possible to switch the imaging module for endoscopes to fabricate the imaging module for endoscopes in which the F-number is different.

Figure 1A:
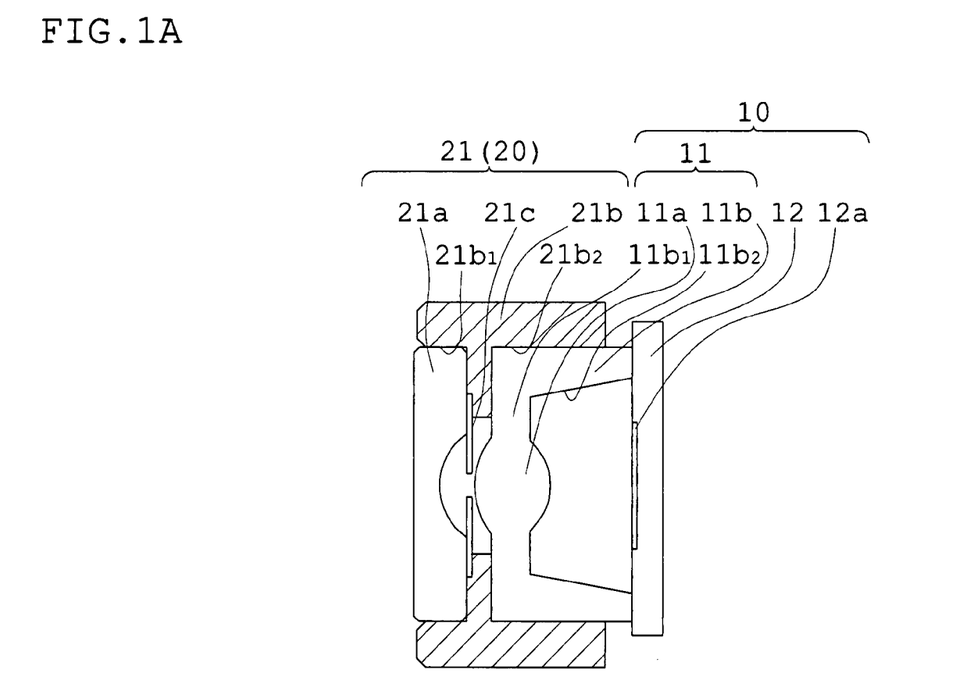
FIG. 1A is an explanatory view showing a schematic structure of the imaging module for endoscopes, with a section developed along the optical axis, according to one embodiment of the present invention in the case where the first optical module is mounted to the fundamental module.
Figure 1B:
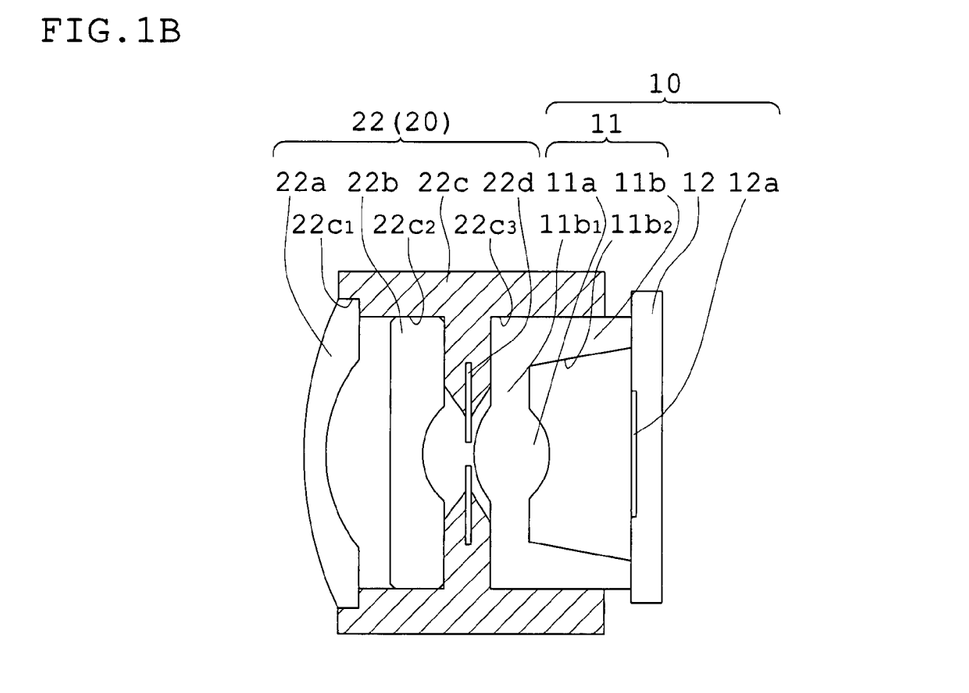
FIG. 1B is an explanatory view showing a schematic structure of the imaging module for endoscopes, with a section developed along the optical axis, according to one embodiment of the present invention in the case where the second optical module is mounted to the fundamental module.

FIGS. 1A and 1B show the schematic structure of the imaging module for endoscopes according to one embodiment of the present invention. FIGS. 2A-2F show various flanges of the convex lens constituting the fundamental module of the imaging module for endoscopes of the embodiment.

The imaging module for endoscopes of the embodiment is constructed to have a fundamental module 10 and a plurality of optical modules 20 that are selectively mountable with respect to the fundamental module 10.

The fundamental module 10 includes a convex lens 11 and image sensor 12.

The convex lens 11 is constructed with a lens section 11$a$ and a flange section 11$b$ that are integrally molded. The lens section 11$a$ is provided with a function of forming an observation image on the surface of the image sensor 12. The flange section 11$b$ has a disc portion 11$b_1$ connected to the periphery of the lens section 11$a$ and a cylinder portion 11$b_2$ connected to the disk portion 11$b_1$ and extending toward the image sensor 12.

The convex lens 11 is such that the end face of the cylinder portion 11$b_2$ of the flange section 11$b$ is cemented to the periphery of an effective imaging region 12$a$ of the image sensor 12 through an adhesive.

The image sensor 12 used may be provided with a cover glass in front of the effective imaging region 12$a$.

When the convex lens 11 is cemented to the image sensor 12, it is necessary to rigidly control the prevention of penetration of dust particles, but even though the dust particles adhere, they can be removed by wiping-off treatment when the cover glass is provided, so that cementation work is sometimes facilitated.

In the cementation between the image sensor 12 and the convex lens 11, for example, the use of a technique of positioning and cementing the image sensor 12 and the convex lens 11 while observing indicators with a camera as in the technique generally used in IC mounting, improves positioning accuracy and reduces the tact time of positioning.

Figure 2A:
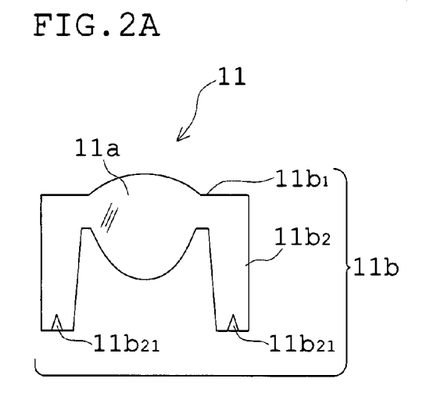
FIG. 2A is a side view showing a convex lens in one example of the flange of the convex lens constituting the fundamental module of the imaging module for endoscopes of the embodiment.
Figure 2B:
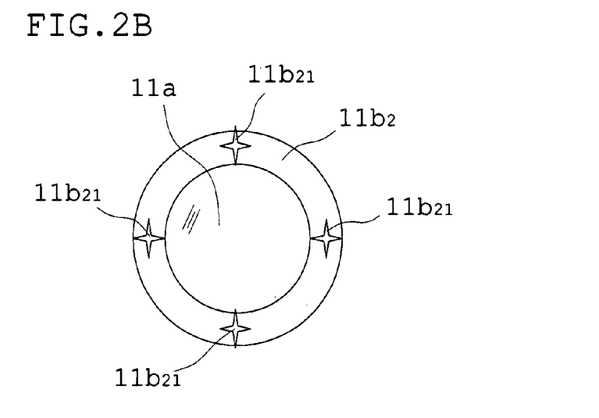
FIG. 2B is a view showing the convex lens according to the example of FIG. 2A, viewed from the lower side.
Figure 2C:
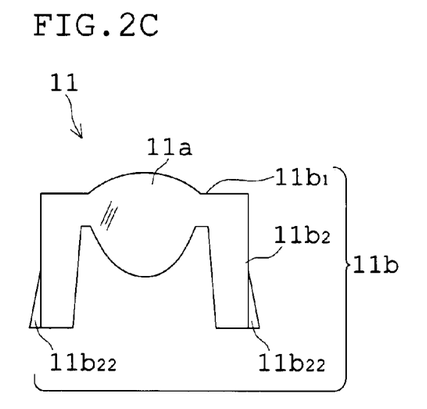
FIG. 2C is a side view showing a convex lens in another example.
Figure 2D:
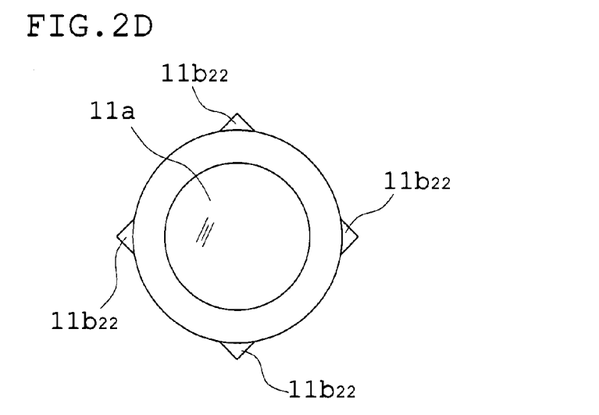
FIG. 2D is a view showing the convex lens according to the example of FIG. 2C, viewed from the lower side.
Figure 2E:
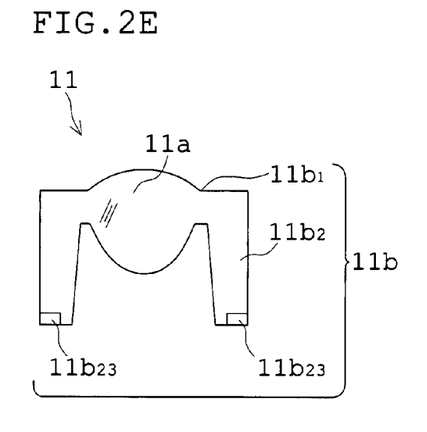
FIG. 2E is a side view showing a convex lens in still another example.
Figure 2F:
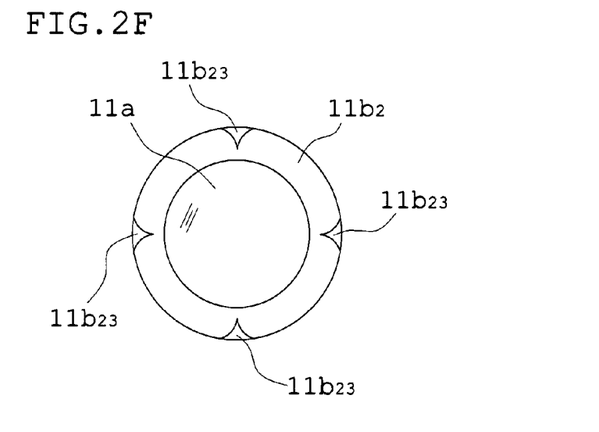
FIG. 2F is a view showing the convex lens according to the example of FIG. 2E, viewed from the lower side.

In this case, it is necessary to provide the indicators with information in horizontal and vertical directions. Thus, as shown in FIGS. 2A and 2B, it is good practice to provide crossed indentations on the end face of the cylinder portion 11$b_2$ of the flange section 11$b$ of the convex lens 11. In the imaging module for endoscopes of this type, however, the edge thickness of the end face of the cylinder portion 11$b_2$ is no more than about 0.3 mm. Thus, as shown in FIGS. 2C and 2D, it is favorable to provide edges that when opposite tops are connected, a cross is obtained, on the peripheral end (the side face) of the cylinder portion 11$b_2$ of the flange section 11$b$ of the convex lens 11. As shown in FIGS. 2E and 2F, it is more favorable to provide arcuate indentations that when opposite tops are connected, a cross is obtained, on the end face of the cylinder portion 11$b_2$ of the convex lens 11, by performing the molding through a remaining part of cutting of the die in milling with a drill.

The plurality of optical modules 20 that are selectively mountable with respect to the fundamental module 10 include a first optical module 21 and a second optical module 22 so that they are selectively switched and can be mounted in front (on the object side) of the fundamental module 10.

The first optical module 21 has a first concave lens 21$a$, a first lens frame 21$b$, and a first aperture stop 21$c$.

The first concave lens 21$a$ is constructed of plastic.

The first lens frame 21$b$ is constructed of a material with a light-blocking property, such as black resin, and has a first lens mounting potion 21$b_1$ and a fundamental module force-fit portion 21$b_2$.

To the first lens mounting portion 21$b_1$, the first concave lens 21$a$ is cemented through an adhesive or is secured by laser fusion.

The fundamental module force-fit portion $21b_2$ is constructed so that the fundamental module 10 can be force-fitted thereinto.

The first aperture stop 21c is interposed between the first concave lens 21a and the lens section 11a of the convex lens 11 and is located at a preset position so that when the first optical module 21 is mounted to the fundamental module 10, an angle of oblique incidence of light of an observation image on the image sensor 12 becomes a preset angle.

Also, FIG. 1A illustrates a state where the first optical module 21 is mounted to the fundamental module 10 in such a way that the flange section 11b is force-fitted into the fundamental module force-fit portion $21b_2$ of the first lens frame 21b.

The second optical module 22 has, in order from the object side, a second concave lens 22a, a third concave lens 22b, a second lens frame 22c, and a second aperture stop 22d, and is different from the first optical module 21 as to the field range attained when the second optical module 22 is mounted to the fundamental module 10.

The second concave lens 22a is constructed of plastic.

The third concave lens 22b is constructed like the first concave lens 21a. By doing so, the number of kinds of optical members is reduced accordingly and thus fabrication can be further simplified.

The second lens frame 22c is constructed of a material with a light-blocking property, such as black resin, and has a second lens mounting portion $22c_1$, a third lens mounting portion $22c_2$, and a fundamental module force-fit portion $22c_3$.

To the third lens mounting portion $22c_2$, the third concave lens 22b is cemented through an adhesive. To the second lens mounting portion $22c_1$, the second concave lens 22a is cemented through an adhesive.

The fundamental module force-fit portion $22c_3$, like the fundamental module force-fit portion $21b_2$, is constructed so that the fundamental module 10 can be force-fitted thereinto.

The second aperture stop 22d is interposed between the third concave lens 22b and the lens section 11a of the convex lens 11 and is located at the position where a distance from the most object-side optical surface of the fundamental module 10 to the second aperture stop 22d, attained when the second optical module 22 is mounted to the fundamental module 10 is the same as in the first aperture stop 21c of the first optical module 21. Further, the second aperture stop 22d is constructed so that when the second optical module 22 is mounted to the fundamental module 10, the angle of oblique incidence of light of the observation image on the image sensor 12 becomes constant as in the first aperture stop 21c where the first optical module 21 is mounted. Whereby, even when either of the optical modules 21 and 22 is mounted to the fundamental module 10, the variation of the angle of oblique incidence can be obviated.

Also, FIG. 1B illustrates a state where the second optical module 22 is mounted to the fundamental module 10 in such a way that the flange section 11b is force-fitted into the fundamental module force-fit portion $22c_3$ of the second lens frame 22c.

In the imaging module for endoscopes of the embodiment, the first lens mounting portion $21b_1$ of the first lens frame 21b and the third lens mounting portion $22c_2$ of the second lens frame 22c are constructed so that even when either the first optical module 21 or the second optical module 22 is mounted to the fundamental module 10, a distance between the image-side surface of the third concave lens 22b and the object-side surface of the lens section 11a of the convex lens 11 where the second optical module 22 is mounted to the fundamental module 10 is different from a distance between the image-side surface of the first concave lens 21a and the object-side surface of the lens section 11a of the convex lens 11 where the first optical module 21 is mounted to the fundamental module 10, to form the observation image on the imaging surface of the image sensor 12. Whereby, even when either of the optical modules 21 and 22 is mounted to the fundamental module 10, the adjustment of the image position becomes unnecessary.

Figure 3:
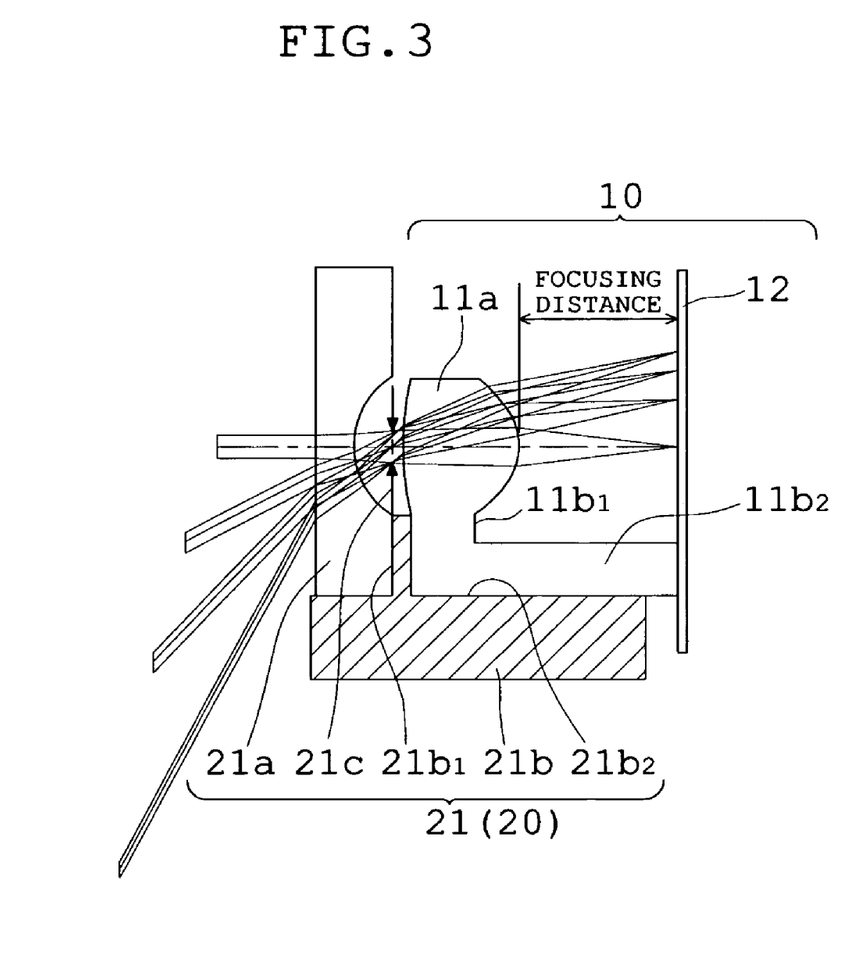
FIG. 3 is a partially sectional view showing essential parts of the imaging module for endoscopes, together with incident rays, developed along the optical axis, which is the same in fundamental optical structure as the imaging module for endoscopes combining the first optical module of the embodiment of FIG. 1A with the fundamental module.
Figure 4:
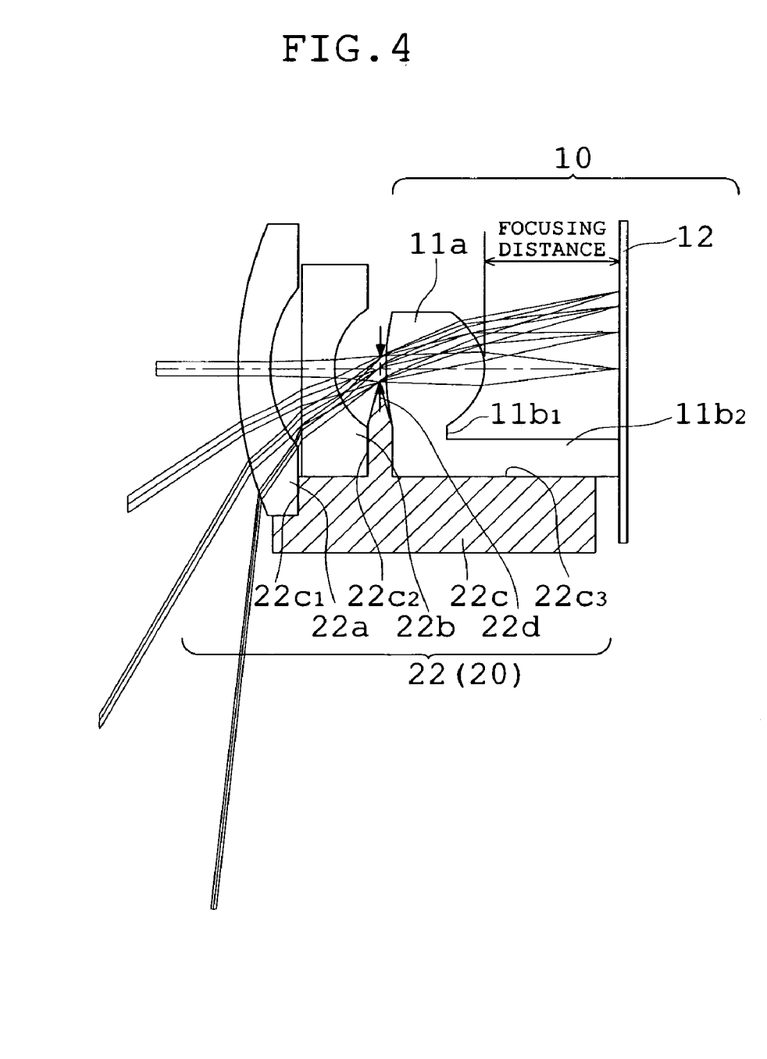
FIG. 4 is a partially sectional view showing essential parts of the imaging module for endoscopes, together with incident rays, developed along the optical axis, which is the same in fundamental optical structure as the imaging module for endoscopes combining the second optical module of the embodiment of FIG. 1B with the fundamental module.

FIG. 3 shows essential parts of the imaging module for endoscopes, together with incident rays, which is the same in fundamental optical structure as the imaging module for endoscopes combining the first optical module of the embodiment of FIG. 1A with the fundamental module. FIG. 4 shows essential parts of the imaging module for endoscopes, together with incident rays, which is the same in fundamental optical structure as the imaging module for endoscopes combining the second optical module of the embodiment of FIG. 1B with the fundamental module. For convenience of illustration, the function and effect of the imaging module for endoscopes of the embodiment will be explained in reference to FIGS. 3 and 4.

According to the imaging module for endoscopes of the embodiment, the fundamental module 10 in which the end face of the flange section 11b of the convex lens 11 is cemented to the image sensor 12 and thereby their mutual positions are fixed is constructed so that it can also be used in the fabrication of the imaging module that the application of observation (a part to be observed) is different, and at the same time, so that in the case where the application of observation (a part to be observed) is different, the optical modules 21 and 22 are selectively mounted to the fundamental module 10 to thereby switch the field range and even when either of the optical modules 21 and 22 is mounted to the fundamental module 10, the image position and the angle of oblique incidence of light of the observation image on the image sensor 12 are practically unchanged. Consequently, the focus adjustment of the rearmost lens can be eliminated.

In the case where the imaging module of the different application of observation is fabricated, the fundamental module 10 is used as a common module and thereby the number of kinds of optical parts to be fabricated can be reduced to a minimum to enable the mass production to be accomplished while applying the high-precision control without increasing the control cost.

Moreover, even when either of the optical modules 21 and 22 is mounted to the fundamental module 10, the angle of oblique incidence of light of the observation image on the image sensor is made practically unchanged. Whereby, the fundamental module using the image sensor of the common specification can be combined with the optical module accommodating the different application of observation (a different part to be observed), and an increase of the fabrication cost caused by developing the image sensor combined in accordance with each individual optical system can be prevented.

According to the imaging module for endoscopes of the embodiment, the fundamental module 10 is force-fitted into each of the fundamental module force-fit portions $21b_2$ and $22c_3$ of the lens frames 21b and 22c of the optical modules 21 and 22 and thereby is fixed. Hence, the direction in which an adhesive is applied can be set in one direction. By doing so, when each of the optical modules 21 and 22 is fixed to the fundamental module 10, there is no need to change the direction of the fundamental module 10 in order to apply the adhesive, and the assembly in an automatic transportation process can be made smooth.

Also, although the imaging module for endoscopes of the embodiment is designed so that the field rang is varied by the changeover in the optical modules 21 and 22, it may be constructed so that the optical modules 21 and 22 are the same in lens arrangement, but differ as to a distance between the most image-side lens surface of each optical module and the object-side surface of the convex lens 11 of the fundamental module 10 where each optical module is mounted to the fundamental module 10.

By doing so, it also becomes possible that the imaging module for endoscopes is fabricated by the changeover to the imaging module for endoscopes in which the field range is the same, but the depth of field is different.

Here, reference is made to the depth of field of the endoscope of the present invention.

Figure 5A:
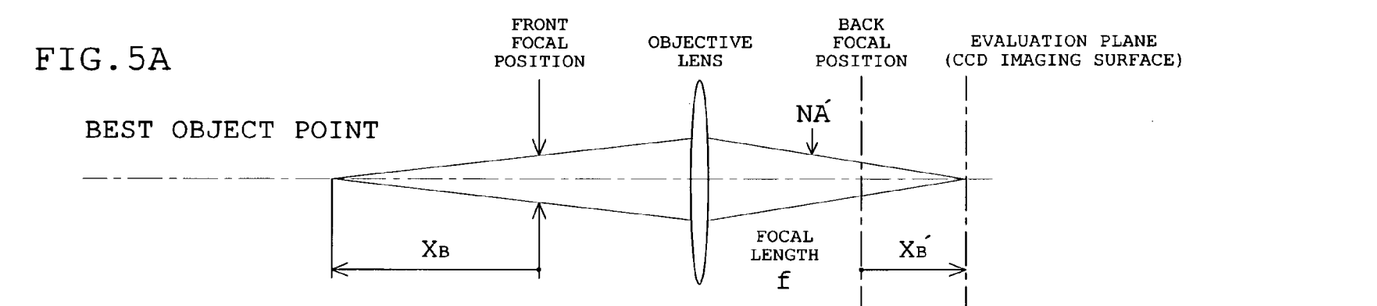
FIGS. 5A, 5B, and 5C are explanatory views showing depths of field of the imaging module for endoscopes in states where light beams are imaged with respect to an evaluation plane (the imaging surface) at the best object point, a near point, and a far point, respectively.
Figure 5B:
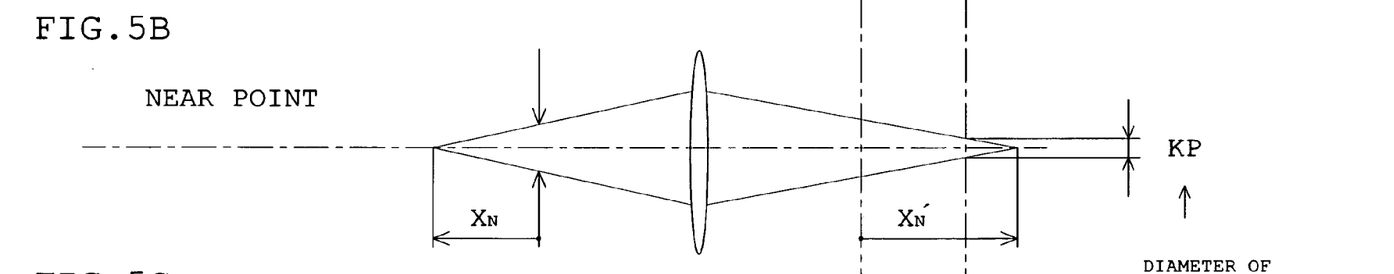
Figure 5C:
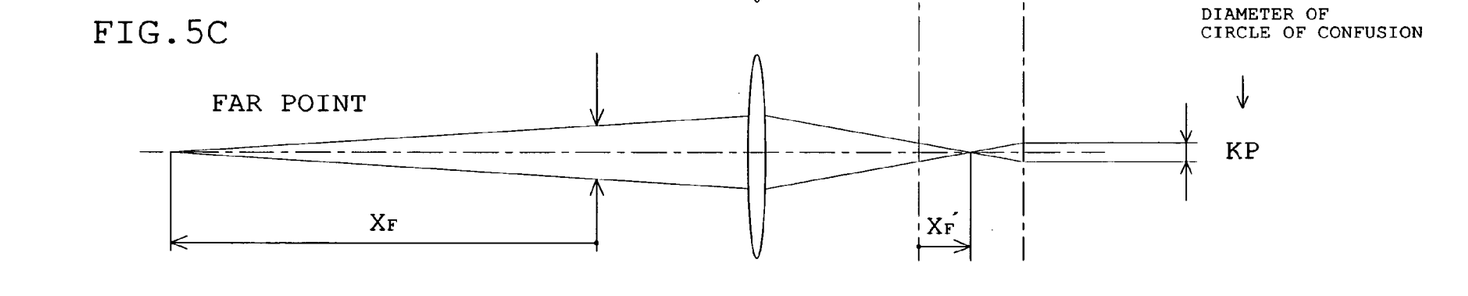

FIGS. 5A-5C show depths of field of the imaging module for endoscopes. As shown in FIGS. 5A-5C, consider the case where a solid-state image sensor of a pixel pitch P is located at an image plane position $X_B'$ where the best distance is $X_B$. On the condition that the solid-state image sensor is fixed, when an object is brought close to a position $X_N$, an image plane position $X_N'$ in this case is shifted from an evaluation position. However, when the diameter of an allowable circle of confusion at an evaluation plane (for example, the surface of the solid-state image sensor such as a CCD) can be recognized to be smaller than a resolution KP of the solid-state image sensor such as a CCD (where K is a coefficient governed by the solid-state image sensor such as a CCD and the characteristic of a circuit system connected to the solid-state image sensor, in which ideally K=2 at a Nyquist rate, but for the convenience of electric processing, a reduction in contrast and the influence of a Kell factor is produced, and thus, actually $2 \leq K \leq 4$), an image of the object located in the range from the position $X_B$ to the position $X_N$ can be thought of as focused. Specifically, the range in which the diameter of the allowable circle of confusion coincides with the resolution KP can be defined as the depth of field on the near point side.

In this case, when the focal length of the optical system is represented by f and an effective aperture of the optical system relative to a finite object point is represented by Fno, from the relationship of the diameter of the circle of confusion, $$2(X_N' - X_B')NA' = KP$$

$$Fno = 1/2NA'$$

From Newton's equation, $$X_N \cdot X_N' = -f^2$$

From the above description, the following equation is established:

Equation on the near point side $$1/X_N - 1/X_B = KP\,Fno/f^2$$

Similarly, the equation on the far point side is defined as $$1/X_B - 1/X_F = KP\,Fno/f^2$$

When these equations are combined, $$1/X_N - 1/X_F = 2KP\,Fno/f^2$$

The range from the position $X_N$ to the position $X_F$, thought of as focused in this case, is defined as the depth of field.

Here, the coefficient K is capable of taking experiential numerical values of about 2-5 in accordance with the image sensor. This calculation is measured by reverse operation on the basis of the experimental value of an actual apparatus.

When a reference surface of the distance is set as the foremost lens surface, it is necessary to reflect a front focal position on the positions $X_N$ and $X_F$.

The imaging module for endoscopes of the embodiment, as mentioned above, may be constructed so that the optical modules 21 and 22, each combined with the fundamental module 10, are the same in lens arrangement, but differ as to a distance between the most image-side lens surface of each optical module and the object-side surface of the convex lens 11 of the fundamental module 10 where each optical module is mounted to the fundamental module 10.

By doing so, as described above, the imaging module for endoscopes can be fabricated by the changeover to the imaging module for endoscopes in which the field range is the same, but the depth of field is different.

In the imaging module for endoscopes of the embodiment, the optical modules 21 and 22 may be designed so that the positions of their aperture stops are different from each other.

By doing so, it becomes possible that the imaging module for endoscopes is fabricated by the changeover to the imaging module for endoscopes that is different in F-number. Also, in this case, the angles of oblique incidence do not strictly coincide, but if they are within a substantially allowable range, the angles of oblique incidence can be handles as almost the same angle and the image sensor of the common specification can be used for the fundamental module.

In accordance with the drawings, the embodiments of the imaging module for endoscopes of the present invention will be explained below. Also, in the drawings of the embodiments described below, only the convex lens and the imaging surface of the image sensor in the fundamental module and the lens and the stop in the optical module are shown, and the flange section of the fundamental module and the lens frame of the optical module are omitted.

Embodiment 1

Figure 6:
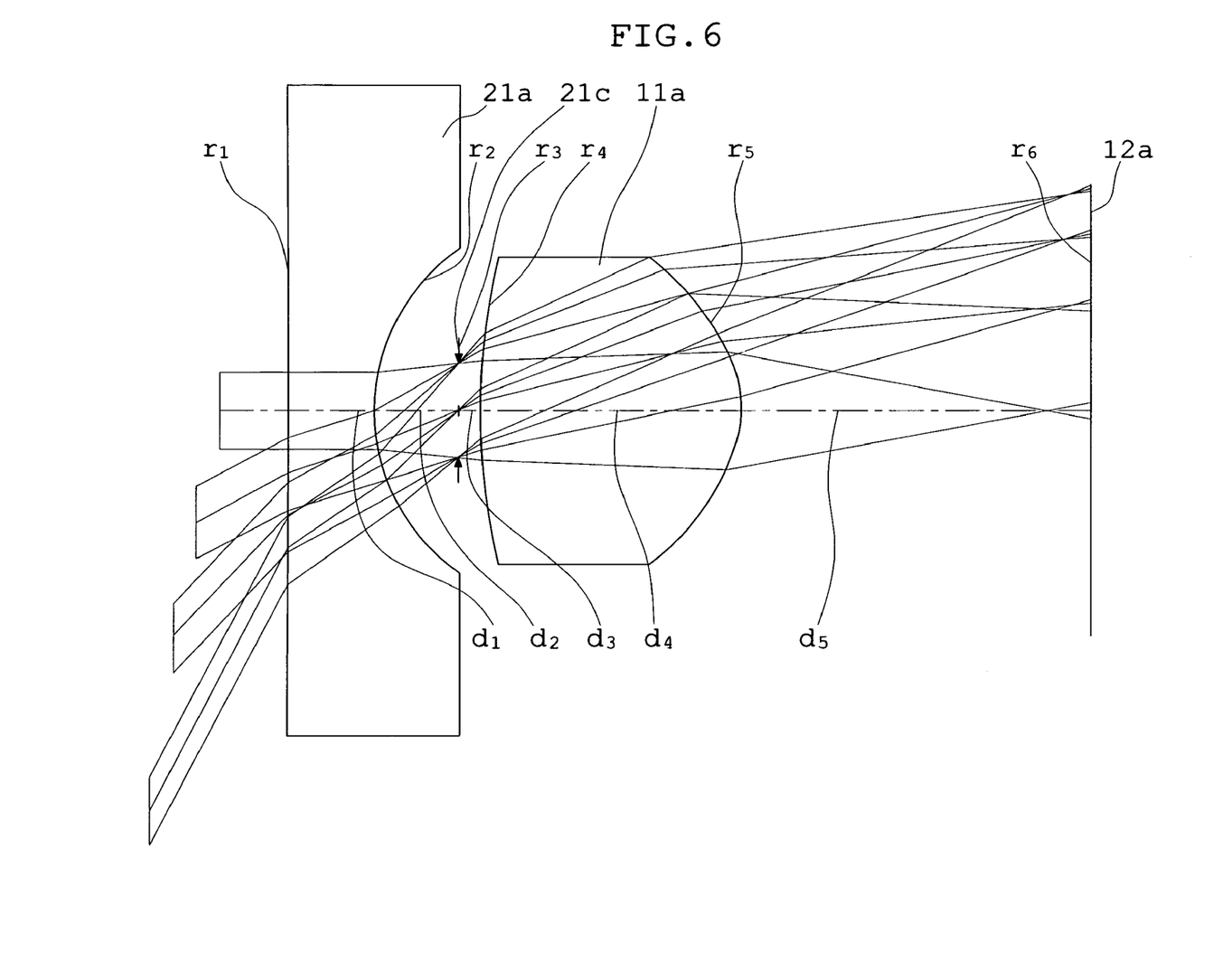
FIG. 6 is a sectional view showing an optical arrangement, developed along the optical axis, in a state where the first optical module is mounted to the fundamental module in the imaging module for endoscopes according to Embodiment 1 of the present invention.
Figure 7:
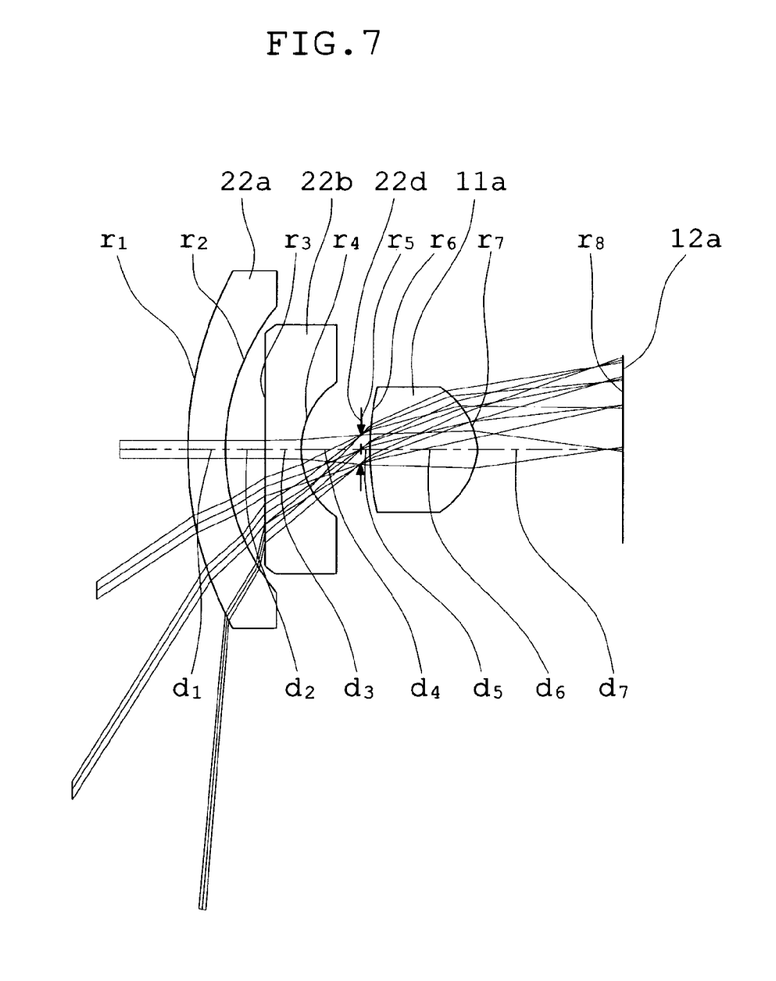
FIG. 7 is a sectional view showing an optical arrangement, developed along the optical axis, in a state where the second optical module is mounted to the fundamental module in the imaging module for endoscopes according to Embodiment 1 of the present invention.

FIG. 6 shows an optical arrangement in a state where the first optical module is mounted to the fundamental module in the imaging module for endoscopes according to Embodiment 1 of the present invention. FIG. 7 shows an optical arrangement in a state where the second optical module is mounted to the fundamental module in the imaging module for endoscopes according to Embodiment 1 of the present invention.

The imaging module for endoscopes of Embodiment 1 has the same fundamental optical arrangement as the imaging module for endoscopes of the embodiment shown in FIGS. 1A, 1B, 3, and 4. In FIG. 6, again, 11a is the lens section of the convex lens 11 in the fundamental module 10, 12a is the effective imaging surface of the image sensor 12 in the fundamental module 10, 21a is the first concave lens in the first optical module 21, and 21c is the first aperture stop in the first optical module 21. In FIG. 7, again, 22a is the second concave lens in the second optical module 22, 22b is the third concave lens in the second optical module 22, and 22d is the second aperture stop in the second optical module 22.

Also, the image-side surface of the lens section 11a of the convex lens 11 is configured into an aspherical shape.

The imaging module for endoscopes in a state shown in FIG. 6 is constructed so that a part to be observed can be imaged on the condition most suitable for the observation of the stomach of a wide space. Specifically, the depth of field is set on the far-point side so that the farthest possible point can be observed. In addition, the imaging module for endoscopes is designed so that when the far point is observed, sufficient brightness can be ensured and the F-number becomes small.

On the other hand, the imaging module for endoscopes in a state shown in FIG. 7 is constructed so that a part to be observed can be imaged on the condition most suitable for is the observation of the intestines of a narrow space. Specifically, a wide angle specification is provided in order to make observation in the widest possible range. Further, the depth of field is set on the near-point side so that a nearby object can be observed. Still further, a stop-down specification is provided because the nearby object observed is bright.

In FIGS. 6 and 7, the fundamental modules 10 are identically constructed. The first concave lens 21a in the first optical module 21 has the same structure as the third concave lens 22b in the second optical module 22.

In either of FIGS. 6 and 7, the imaging position and the angle of oblique incidence of light of the observation image on the effective imaging surface of the image sensor 12 are unchanged.

Subsequently, numerical data of optical members constituting the imaging module for endoscopes of Embodiment 1 are shown below. In the numerical data, $S_1, S_2, \ldots$ denote surface numbers of optical members constituting the imaging module for endoscopes; $r_1, r_2, \ldots$ denote radii of curvature of optical members constituting the imaging module for endoscopes; $d_1, d_2,$ denote spacings between surfaces of optical members constituting the imaging module for endoscopes; $n_{d1}, n_{d2}, \ldots$ denote refractive indices of optical members constituting the imaging module for endoscopes at the d line; and $v_{d1}, v_{d2}, \ldots$ denote Abbe's numbers of optical members constituting the imaging module for endoscopes at the d line. These symbols are also used for other embodiments to be described later.

Also, when Z is taken as the coordinate in the direction of the optical axis, Y is taken as the coordinate normal to the optical axis, k represents a conic constant, and $A_4, A_6, A_8,$ and $A_{10}$ represent aspherical coefficients, the configuration of an aspherical surface is expressed by the following equation:

$$Z=(Y^2/r)/[1+\{1-(1+k)\cdot(Y/r)^2\}^{1/2}]+A_4y^4+A_6y^6+A_8y^8+A_{10}y^{10}\ldots$$

Numerical data 1 (Embodiment 1: Structure in which the first optical module is mounted to the fundamental module)

| | | | | |
|---|---|---|---|---|
| $S_0$ (object surface) | $r_0 = \infty$ | $d_0 = 27.0000$ | | |
| $S_1$ | $r_1 = \infty$ | $d_1 = 0.3890$ | $n_{d1} = 1.51157$ | $v_{d1} = 56.00$ |
| $S_2$ | $r_2 = 0.9218$ | $d_2 = 0.3890$ | | |
| $S_3$ (stop) | $r_3 = \infty$ | $d_3 = 0.1037$ | | |
| $S_4$ | $r_4 = 3.4792$ | $d_4 = 1.1670$ | $n_{d4} = 1.58874$ | $v_{d4} = 30.49$ |
| $S_5$ | $r_5 = -0.6693$ | $d_5 = 1.5594$ | | |
| $S_6$ (imaging surface) | $r_6 = \infty$ | | | |

Aspherical coefficients
Fifth surface $k = -2.4451$
$A_2 = 0 \quad A_4 = -7.1662 \times 10^{-1} \quad A_6 = 4.6697 \times 10^{-1} \quad A_8 = 0 \quad A_{10} = 0$

| | |
|---|---|
| F-number: | 2.78 |
| Near point: | 16 |
| Best object point: | 27 |
| Far point: | 82 |
| Focal length: | 1 |
| Front focal distance: | 0.366 |
| Pixel pitch P: | 2.2 um |
| Coefficient K where resolution of the image sensor is KP: | 4 |
| Field angle: | 126.68 |
| Angle of oblique incidence: | −14.727 |

Numerical data 2 (Embodiment 1: Structure in which the second optical module is mounted to the fundamental module. Field angle, focus point, and Fno are changed.)

| | | | | |
|---|---|---|---|---|
| $S_0$ (object surface) | $r_0 = \infty$ | $d_0 = 12.0000$ | | |
| $S_1$ | $r_1 = 4.4407$ | $d_1 = 0.3890$ | $n_{d1} = 1.51157$ | $v_{d1} = 56.00$ |
| $S_2$ | $r_2 = 2.2631$ | $d_2 = 0.4174$ | | |
| $S_3$ (stop) | $r_3 = \infty$ | $d_3 = 0.3890$ | $n_{d3} = 1.51157$ | $v_{d3} = 56.00$ |
| $S_4$ | $r_4 = 0.9218$ | $d_4 = 0.6533$ | | |
| $S_5$ | $r_5 = \infty$ | $d_5 = 0.1037$ | | |
| $S_6$ | $r_6 = 3.4792$ | $d_6 = 1.1670$ | $n_{d6} = 1.58874$ | $v_{d6} = 30.49$ |
| $S_7$ | $r_7 = -0.6693$ | $d_7 = 1.5594$ | | |
| $S_8$ (imaging surface) | $r_8 = \infty$ | | | |

Aspherical coefficients
Seventh surface $k = -2.4451$
$A_2 = 0 \quad A_4 = -7.1662 \times 10^{-1} \quad A_6 = 4.6697 \times 10^{-1} \quad A_8 = 0 \quad A_{10} = 0$

| | |
|---|---|
| F-number: | 3.64 |
| Near point: | 7 |
| Best object point: | 12 |
| Far point: | 32 |
| Focal length: | 0.842 |
| Front focal distance: | 1.242 |
| Pixel pitch P: | 2.2 um |
| Coefficient K where resolution of the image sensor is KP: | 4 |
| Field angle: | 171.33 |
| Angle of oblique incidence: | −14.727 |

Embodiment 2

Figure 8:
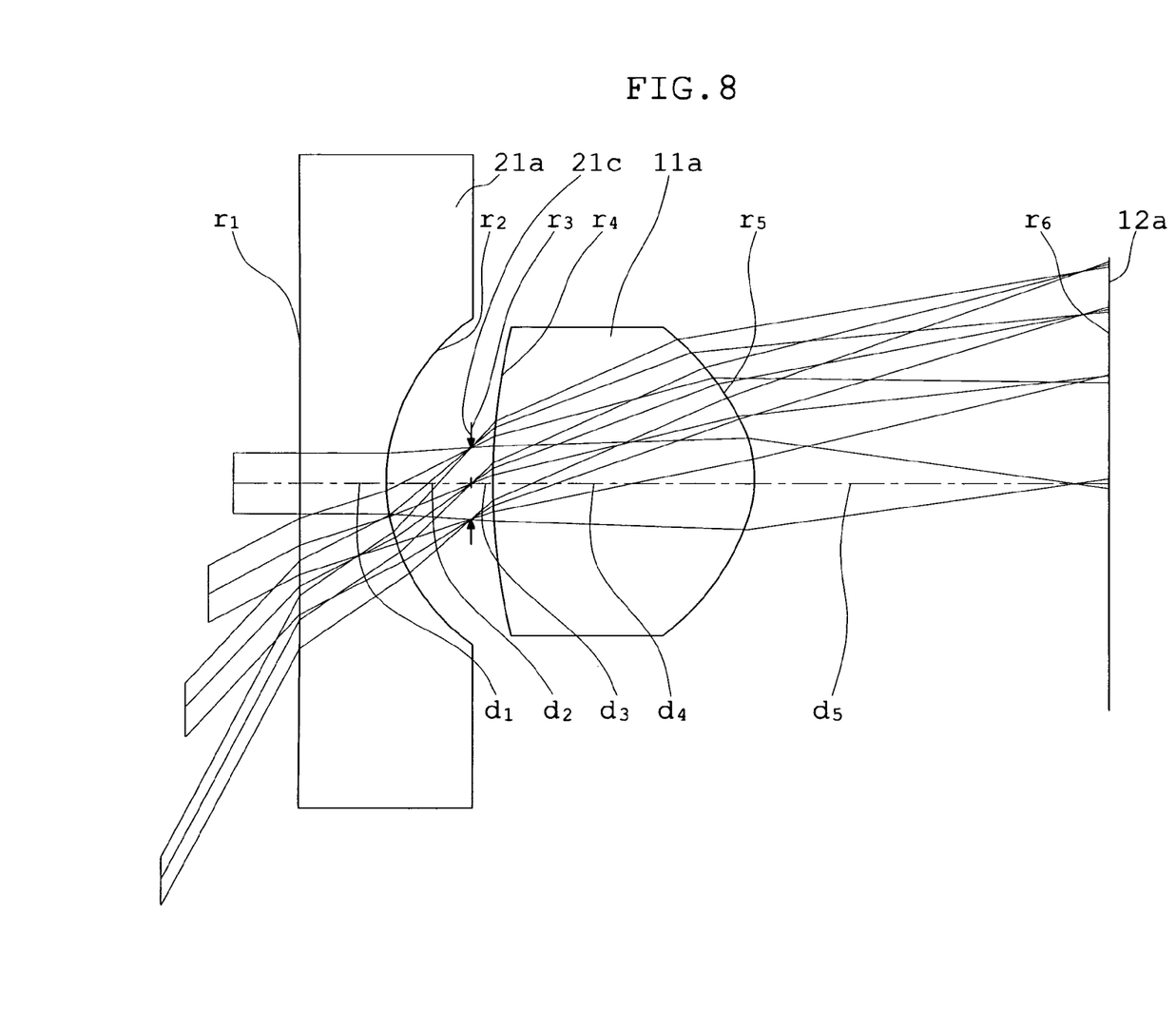
FIG. 8 is a sectional view showing an optical arrangement, developed along the optical axis, in a state where the first optical module is mounted to the fundamental module in the imaging module for endoscopes according to Embodiment 2 of the present invention.
Figure 9:
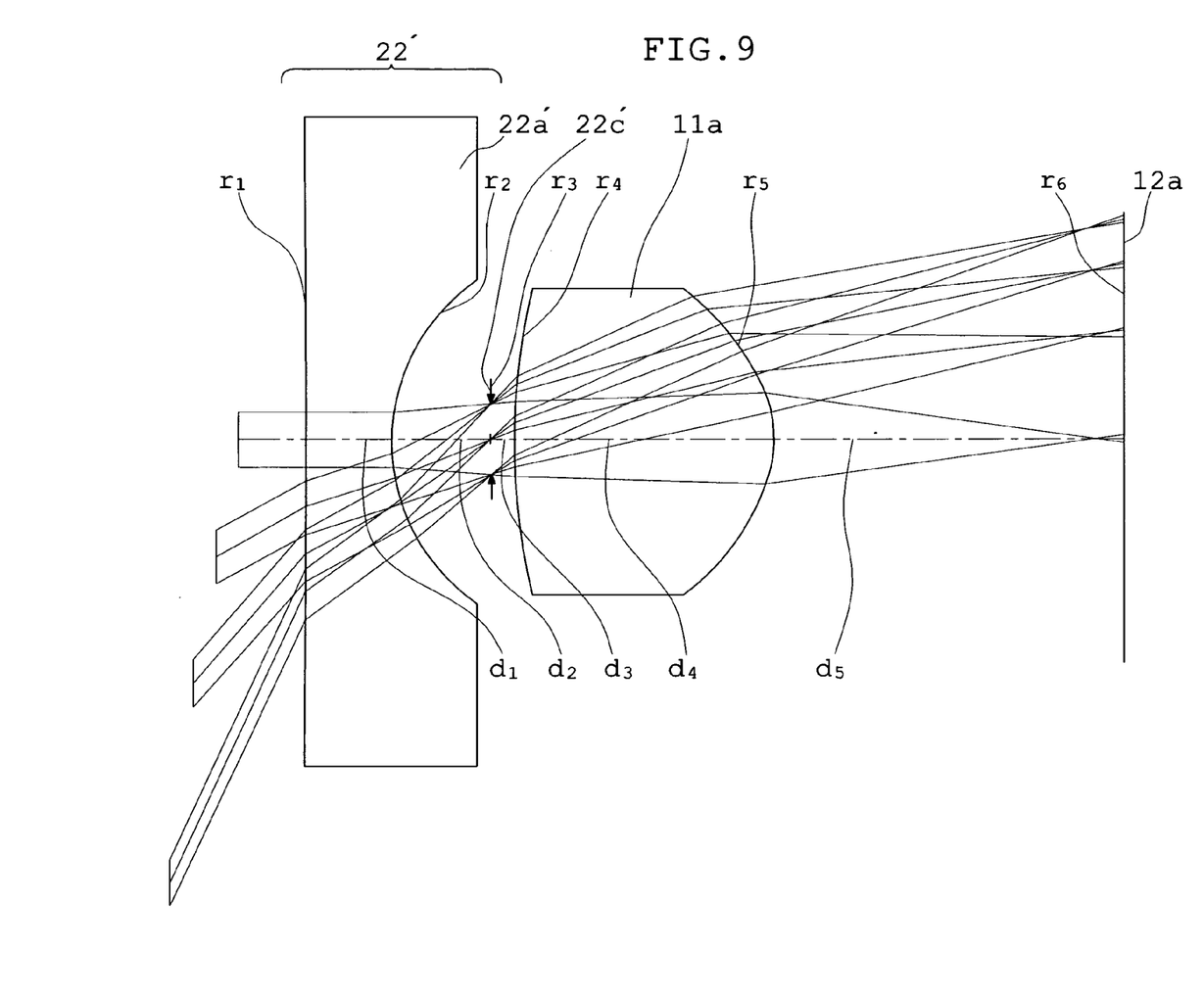
FIG. 9 is a sectional view showing an optical arrangement, developed along the optical axis, in a state where the second optical module is mounted to the fundamental module in the imaging module for endoscopes according to Embodiment 2 of the present invention.
Figure 10:
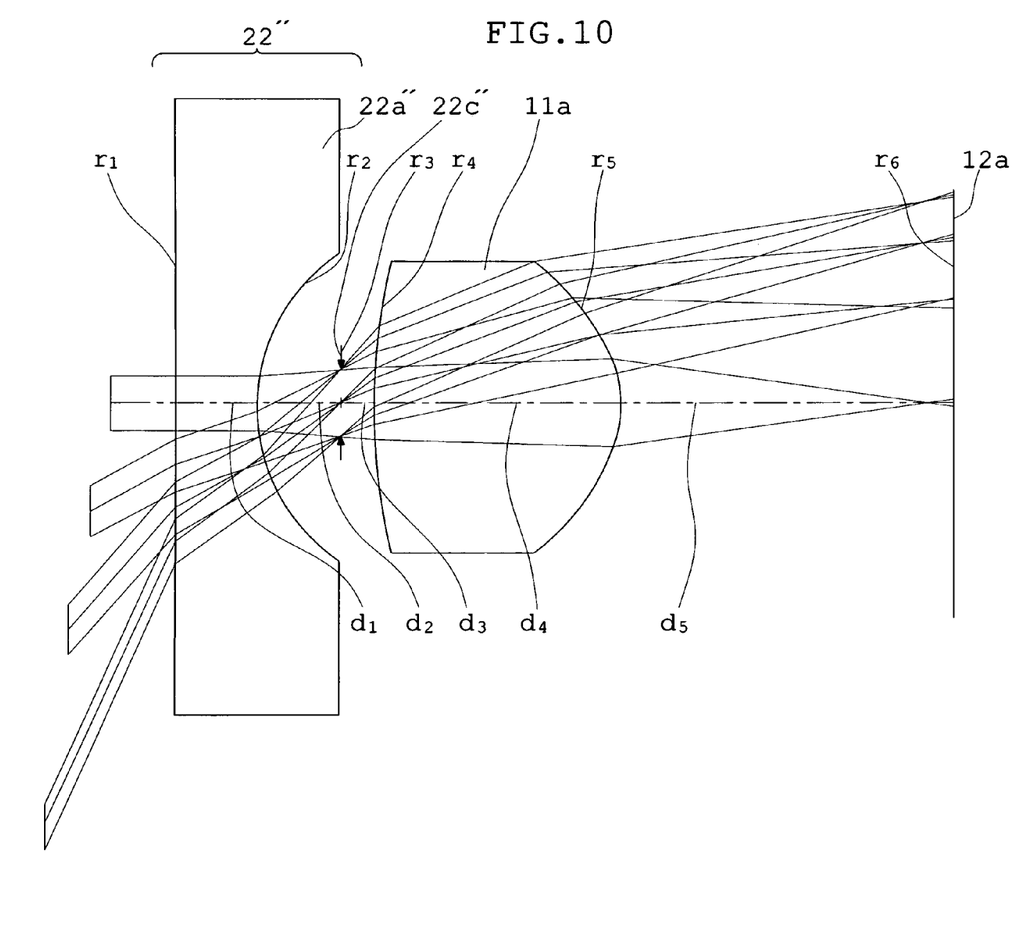
FIG. 10 is a sectional view showing an optical arrangement, developed along the optical axis, in a state where a modified example of the second optical module is mounted to the fundamental module in the imaging module for endoscopes according to Embodiment 2 of the present invention.

FIG. 8 shows an optical arrangement in a state where the first optical module is mounted to the fundamental module in the imaging module for endoscopes according to Embodiment 2 of the present invention. FIG. 9 shows an optical arrangement in a state where the second optical module is mounted to the fundamental module in the imaging module for endoscopes according to Embodiment 2 of the present invention. FIG. 10 shows an optical arrangement in a state where a modified example of the second optical module is mounted to the fundamental module in the imaging module for endoscopes according to Embodiment 2 of the present invention.

The imaging module for endoscopes of Embodiment 2, as shown in FIG. 8, has the same fundamental optical arrangement as the imaging module for endoscopes of the embodiment shown in FIGS. 1A and 3 with respect to the fundamental module and the first optical module. In FIG. 8, again, 11a is the lens section of the convex lens 11 in the fundamental module 10, 12a is the effective imaging surface of the image sensor 12 in the fundamental module 10, 21a is the first concave lens in the first optical module 21, and 21c is the first aperture stop in the first optical module 21.

In the second optical module, as shown in FIG. 9, the second lens frame is constructed so that spacing between the image-side surface of the second concave lens and the object-side surface of the convex lens is different from spacing between the image-side surface of the first concave lens 21a and the object-side surface of the convex lens 11 where the first optical module 21 is mounted to the fundamental module 10. Other features are nearly the same as in the first optical module 21 of FIG. 8. In FIG. 9, reference numeral 22a' denotes a second concave lens in a second optical module 22' and 22c' denotes a second aperture stop in the second optical module 22'.

In the second optical module according to the modified example, as shown in FIG. 10, the second lens frame is constructed so that spacing between the image-side surface of the second concave lens and the object-side surface of the convex lens is different from spacing between the image-side surface of the first concave lens 21*a* and the object-side surface of the convex lens 11 where the first optical module 21 is mounted to the fundamental module 10 and at the same time, the position of the second aperture stop is different from the position of the second aperture stop 21*c* in the first optical module 21. Other features are nearly the same as in the first optical module 21 of FIG. 8. In FIG. 10, reference numeral 22*a*" denotes a second concave lens in a second optical module 22" according to the modified example and 22*c*" denotes a second aperture stop in the second optical module 22" according to the modified example.

Also, the image-side surface of the lens section 11*a* of the convex lens 11 is configured into an aspherical shape.

The imaging module for endoscopes shown in FIG. 8 is constructed by making standard optical setting as the endoscope.

In contrast to this, the imaging module for endoscopes shown in FIG. 9 is constructed by making the optical setting in which the depth of field is provided to approach the object side so that the nearby object is more easily observed.

Further, the imaging module for endoscopes shown in FIG. 10 is such that, in addition to the arrangement of FIG. 9, the second aperture stop 22*c*" is located at a position different from the positions in FIGS. 8 and 9.

In FIGS. 8-10, the fundamental modules 10 are identically constructed. The first concave lens 21*a* in the first optical module 21 has the same structure as the second concave lens 22*a* in the second optical module 22.

In any of FIGS. 8-10, the imaging position and the angle of oblique incidence of light of the observation image on the effective imaging surface of the image sensor 12 are practically unchanged.

Subsequently, numerical data of optical members constituting the imaging module for endoscopes of Embodiment 2 are shown below.

Numerical data 3 (Embodiment 2: fundamental aspect)

| | | | | |
|---|---|---|---|---|
| $S_0$ (object surface) | $r_0 = \infty$ | $d_0 = 22.0000$ | | |
| $S_1$ | $r_1 = \infty$ | $d_1 = 0.3890$ | $n_{d1} = 1.51157$ | $v_{d1} = 56.00$ |
| $S_2$ | $r_2 = 0.9218$ | $d_2 = 0.3890$ | | |
| $S_3$ (stop) | $r_3 = \infty$ | $d_3 = 0.1037$ | | |
| $S_4$ | $r_4 = 3.4792$ | $d_4 = 1.1670$ | $n_{d4} = 1.58874$ | $v_{d4} = 30.49$ |
| $S_5$ | $r_5 = -0.6693$ | $d_5 = 1.5675$ | | |
| $S_6$ (imaging surface) | $r_6 = \infty$ | | | |

Aspherical coefficients
Fifth surface $k = -2.4451$
$A_2 = 0 \quad A_4 = -7.1662 \times 10^{-1} \quad A_6 = 4.6697 \times 10^{-1} \quad A_8 = 0 \quad A_{10} = 0$

| | |
|---|---|
| F-number: | 3.6 |
| Near point: | 12.7 |
| Best object point: | 22 |
| Far point: | 78.4 |
| Focal length: | 1 |
| Front focal distance: | 0.366 |
| Pixel pitch P: | 2.2 um |
| Coefficient K where resolution of the image sensor is KP: | 4 |
| Field angle: | 126.29 |
| Angle of oblique incidence: | −14.691 |

Numerical data 4 (Embodiment 2: near point focus, fixed stop position)

| | | | | |
|---|---|---|---|---|
| $S_0$ (object surface) | $r_0 = \infty$ | $d_0 = 15.0000$ | | |
| $S_1$ | $r_1 = \infty$ | $d_1 = 0.3890$ | $n_{d1} = 1.51157$ | $v_{d1} = 56.00$ |
| $S_2$ | $r_2 = 0.9218$ | $d_2 = 0.4445$ | | |
| $S_3$ (stop) | $r_3 = \infty$ | $d_3 = 0.1037$ | | |
| $S_4$ | $r_4 = 3.4792$ | $d_4 = 1.1670$ | $n_{d4} = 1.58874$ | $v_{d4} = 30.49$ |
| $S_5$ | $r_5 = -0.6693$ | $d_5 = 1.5675$ | | |
| $S_6$ (imaging surface) | $r_6 = \infty$ | | | |

Aspherical coefficients
Fifth surface $k = -2.4451$
$A_2 = 0 \quad A_4 = -7.1662 \times 10^{-1} \quad A_6 = 4.6697 \times 10^{-1} \quad A_8 = 0 \quad A_{10} = 0$

| | |
|---|---|
| F-number: | 3.6 |
| Near point: | 9.7 |
| Best object point: | 15 |
| Far point: | 32 |
| Focal length: | 0.972 |
| Front focal distance: | 0.414 |
| Pixel pitch P: | 2.2 um |
| Coefficient K where resolution of the image sensor is KP: | 4 |
| Field angle: | 131.74 |
| Angle of oblique incidence: | −14.691 |

Numerical data 5 (Embodiment 2: near point focus, changed stop position)

| | | | | |
|---|---|---|---|---|
| $S_0$ (object surface) | $r_0 = \infty$ | $d_0 = 15.0000$ | | |
| $S_1$ | $r_1 = \infty$ | $d_1 = 0.3890$ | $n_{d1} = 1.51157$ | $v_{d1} = 56.00$ |
| $S_2$ | $r_2 = 0.9218$ | $d_2 = 0.3890$ | | |
| $S_3$ (stop) | $r_3 = \infty$ | $d_3 = 0.1592$ | | |
| $S_4$ | $r_4 = 3.4792$ | $d_4 = 1.1670$ | $n_{d4} = 1.58874$ | $v_{d4} = 30.49$ |
| $S_5$ | $r_5 = -0.6693$ | $d_5 = 1.5675$ | | |
| $S_6$ (imaging surface) | $r_6 = \infty$ | | | |

Aspherical coefficients
Fifth surface $k = -2.4451$
$A_2 = 0 \quad A_4 = -7.1662 \times 10^{-1} \quad A_6 = 4.6697 \times 10^{-1} \quad A_8 = 0 \quad A_{10} = 0$

| | |
|---|---|
| F-number: | 3.54 |
| Near point: | 9.8 |
| Best object point: | 15 |
| Far point: | 31 |
| Focal length: | 0.972 |
| Front focal distance: | 0.414 |
| Pixel pitch P: | 2.2 um |
| Coefficient K where resolution of the image sensor is KP: | 4 |
| Field angle: | 132.83 |
| Angle of oblique incidence: | −13.03 |

In general, as mentioned above, the imaging module for endoscopes of the present invention has the following features.

(1) In the imaging module for endoscopes, each individual optical module that is selectively mountable with respect to the fundamental module is constructed so that spacing between the most image-side lens surface in the optical module and the most object-side lens surface in the fundamental module where the optical module is mounted to the fundamental module is varied and thereby the image position of light of the observation image on the image sensor is practically unchanged.

(2) In the imaging module for endoscopes set forth in Item (1), each individual optical module that is selectively mountable with respect to the fundamental module has the aperture stop interposed between the most image-side lens surface in the optical module and the most object-side lens surface in the fundamental module where the optical module is mounted to the fundamental module, and is constructed so that the angle of oblique incidence of light of the observation image on the image sensor through the aperture stop is practically unchanged.

(3) In the imaging module for endoscopes set forth in Item (1) or (2), each individual optical module that is selectively mountable with respect to the fundamental module is constructed so that any convex lens in the optical module is cemented to the lens frame made of black resin or is secured by laser fusion.

(4) In the imaging module for endoscopes set forth in any one of Item (1)-(3), each individual optical module that is selectively mountable with respect to the fundamental module provides the lens frame made of black resin in the optical module with the fundamental module force-fit portion and is fixedly mounted to the fundamental module by force-fitting the fundamental module into the fundamental module force-fit portion.

(5) In the imaging module for endoscopes set forth in any one of Items (1)-(4), the convex lens is a molded lens of plastic, has a flange abutting on the image sensor, and provides marking that allows position control in horizontal and vertical directions with the end face of the flange abutting on the image sensor.

(6) In the imaging module for endoscopes set forth in Item (5), the marking has arcuate portions by milling.

The imaging module for endoscopes of the present invention is useful in the field of medicine that uses disposable compact endoscopes, such as capsule endoscopes, requiring low costs and popularization.

What is claimed is:

1. An imaging module for endoscopes comprising:
a fundamental module including a convex lens and an image sensor that are fixedly positioned relative to one another; and
an optical module selected among a plurality of optical modules each of which is constructed to be mountable to the fundamental module, the imaging module being formed by mounting the selected optical module to the fundamental module,
wherein an observation condition is switched in accordance with the selected optical module mounted to the fundamental module, and
wherein an image position and an angle of oblique incidence of light of an observation image on the image sensor are practically unchanged irrespective of which one of the plurality of optical modules is mounted on the fundamental module.

2. An imaging module for endoscopes according to claim 1, wherein the plurality of optical modules have a first optical module including a first concave lens made of plastic and a first lens frame made of black resin, positioning and retaining the first concave lens; and a second optical module including, in order from an object side, a second concave lens made of plastic, a third concave lens constructed similar to the first concave lens, and a second lens frame made of black resin, positioning and retaining the second concave lens and the third concave lens, the second lens frame being constructed so that spacing between an image-side surface of the third concave lens and an object-side surface of the convex lens of the fundamental module where the second optical module is mounted to the fundamental module is different from spacing between the image-side surface of the first concave lens and the object-side surface of the convex lens of the fundamental module where the first optical module is mounted to the fundamental module, to be selectively mountable with respect to the fundamental module.

3. An imaging module for endoscopes according to claim 1, wherein the plurality of optical modules have a first optical module including a first concave lens made of plastic and a first lens frame made of black resin, positioning and retaining the first concave lens; and a second optical module including a second concave lens constructed similar to the first concave lens and a second lens frame made of black resin, positioning and retaining the second concave lens, the second lens frame being constructed so that spacing between an image-side surface of the second concave lens and an object-side surface of the convex lens of the fundamental module where the second optical module is mounted to the fundamental module is different from spacing between the image-side surface of the first concave lens and the object-side surface of the convex lens of the fundamental module where the first optical module is mounted to the fundamental module, to be selectively mountable with respect to the fundamental module.

4. An imaging module for endoscopes according to claim 1, wherein the plurality of optical modules have a first optical module including a first concave lens made of plastic and a first lens frame made of black resin provided with a first aperture stop, positioning and retaining the first concave lens; and a second optical module including a second concave lens constructed similar to the first concave lens and a second lens frame made of black resin provided with a second aperture stop different in location from the first aperture stop, to be selectively mountable with respect to the fundamental module.

* * * * *